(12) United States Patent
Bennett

(10) Patent No.: US 11,013,504 B2
(45) Date of Patent: May 25, 2021

(54) MEDICAL DEVICE FOR WOUND CLOSURE AND METHOD OF USE

(71) Applicant: Covidien LP, Mansfield, MA (US)

(72) Inventor: Steven Bennett, Cheshire, CT (US)

(73) Assignee: COVIDIEN LP, Mansfield, MA (US)

( * ) Notice: Subject to any disclaimer, the term of this patent is extended or adjusted under 35 U.S.C. 154(b) by 439 days.

(21) Appl. No.: 15/918,259

(22) Filed: Mar. 12, 2018

(65) Prior Publication Data

US 2018/0199930 A1 Jul. 19, 2018

Related U.S. Application Data

(62) Division of application No. 12/511,462, filed on Jul. 29, 2009, now Pat. No. 9,943,302.

(Continued)

(51) Int. Cl.
*A61B 17/04* (2006.01)
*A61B 17/06* (2006.01)

(52) U.S. Cl.
CPC .. *A61B 17/0401* (2013.01); *A61B 2017/0404* (2013.01); *A61B 2017/0417* (2013.01); *A61B 2017/0446* (2013.01); *A61B 2017/0461* (2013.01); *A61B 2017/0462* (2013.01); *A61B 2017/0464* (2013.01); *A61B 2017/06176* (2013.01)

(58) Field of Classification Search
CPC ............ A61B 17/0487; A61B 17/0401; A61B 17/0057; A61B 2017/0404; A61B 2017/0464; A61B 2017/0417; A61B 2017/00659; A61B 2017/00004; A61B 2017/00654; A61B 2017/00637; A61B 2017/06176; A61B 2017/0419; A61B 2017/0403; A61B 2017/0406; A61B 2017/0408; A61B 2017/0414; A61B 2017/0446; A61B 2017/0448; A61B 2017/045; A61B 2017/0451; A61B 2017/0454; A61B 2017/0456; A61B 2017/0461; A61B 2017/0462
See application file for complete search history.

(56) References Cited

U.S. PATENT DOCUMENTS 3,123,077 A 3/1964 Alcamo
4,007,743 A * 2/1977 Blake ................. A61B 17/0057
606/232

(Continued)

FOREIGN PATENT DOCUMENTS

EP 0513736 A1 11/1992
EP 1704878 A2 9/2006
(Continued)

OTHER PUBLICATIONS

Extended European Search Report corresponding to EP 14 16 4895.6, dated Dec. 16, 2014; (12 pp).

(Continued)

*Primary Examiner* — Dianne Dornbusch

(57) ABSTRACT

A medical device for wound closure, e.g., repairing perforations and tissue wall defects. The medical device has a barbed elongate body and an outer member. The medical device may further include a foam structure. The medical device may also include an inner member which may be a tissue scaffold. A method for closing tissue is also disclosed.

13 Claims, 3 Drawing Sheets

Related U.S. Application Data

(60) Provisional application No. 61/088,145, filed on Aug. 12, 2008.

(56) References Cited

U.S. PATENT DOCUMENTS

| | | | |
|---|---|---|---|
| 4,235,238 A | 11/1980 | Ogiu et al. | |
| 4,705,040 A | 11/1987 | Mueller et al. | |
| 4,744,364 A | 5/1988 | Kensey | |
| 5,269,809 A | 12/1993 | Hayhurst et al. | |
| 5,342,393 A * | 8/1994 | Stack | A61B 17/0057 24/453 |
| 5,350,399 A * | 9/1994 | Erlebacher | A61B 17/0057 128/899 |
| 5,370,661 A | 12/1994 | Branch | |
| 5,531,759 A | 7/1996 | Kensey et al. | |
| 5,545,178 A | 8/1996 | Kensey et al. | |
| 5,549,633 A | 8/1996 | Evans et al. | |
| 5,593,422 A | 1/1997 | Muijs Van de Moer et al. | |
| 5,620,461 A | 4/1997 | Muijs Van De Moer et al. | |
| 5,669,935 A | 9/1997 | Rosenman et al. | |
| 5,681,334 A | 10/1997 | Evans et al. | |
| 5,700,277 A * | 12/1997 | Nash | A61B 17/0057 128/887 |
| 5,725,556 A * | 3/1998 | Moser | A61B 17/0487 128/898 |
| 5,916,236 A | 6/1999 | Muijs Van de Moer et al. | |
| 6,007,563 A | 12/1999 | Nash et al. | |
| 6,022,351 A * | 2/2000 | Bremer | A61B 17/688 606/324 |
| 6,174,322 B1 * | 1/2001 | Schneidt | A61B 17/0057 606/213 |
| 6,270,515 B1 * | 8/2001 | Linden | A61B 17/0057 606/213 |
| 6,280,474 B1 | 8/2001 | Cassidy et al. | |
| 6,306,159 B1 | 10/2001 | Schwartz et al. | |
| 6,312,446 B1 * | 11/2001 | Huebsch | A61B 17/0057 606/157 |
| 6,322,580 B1 | 11/2001 | Kanner | |
| 6,348,064 B1 | 2/2002 | Kanner | |
| 6,462,169 B1 | 10/2002 | Shalaby | |
| 6,491,714 B1 * | 12/2002 | Bennett | A61F 2/0805 606/232 |
| 6,506,190 B1 | 1/2003 | Walshe | |
| 6,508,828 B1 | 1/2003 | Akerfeldt et al. | |
| 6,514,534 B1 | 2/2003 | Sawhney | |
| 6,533,762 B2 | 3/2003 | Kanner et al. | |
| 6,566,406 B1 | 5/2003 | Pathak et al. | |
| 6,569,081 B1 * | 5/2003 | Nielsen | A61F 2/0009 600/32 |
| 6,596,013 B2 * | 7/2003 | Yang | A61B 17/0057 606/139 |
| 6,605,294 B2 | 8/2003 | Sawhney | |
| 6,669,707 B1 * | 12/2003 | Swanstrom | A61B 17/0643 606/151 |
| 6,703,047 B2 | 3/2004 | Sawhney et al. | |
| 6,773,450 B2 | 8/2004 | Leung et al. | |
| 6,794,485 B2 | 9/2004 | Shalaby et al. | |
| 6,818,018 B1 | 11/2004 | Sawhney | |
| 6,860,895 B1 * | 3/2005 | Akerfeldt | A61B 17/0057 606/139 |
| 7,009,034 B2 | 3/2006 | Pathak et al. | |
| 7,021,316 B2 | 4/2006 | Leiboff | |
| 7,026,437 B2 | 4/2006 | Shalaby et al. | |
| 7,056,333 B2 | 6/2006 | Walshe | |
| 7,070,858 B2 | 7/2006 | Shalaby et al. | |
| 7,129,319 B2 | 10/2006 | Shalaby | |
| 7,169,168 B2 | 1/2007 | Muijs Van De Moer et al. | |
| 7,182,763 B2 | 2/2007 | Nardella | |
| 7,250,057 B2 | 7/2007 | Forsberg | |
| 7,288,105 B2 | 10/2007 | Oman et al. | |
| 7,347,850 B2 | 3/2008 | Sawhney | |
| 7,416,554 B2 | 8/2008 | Lam et al. | |
| 7,758,594 B2 | 7/2010 | Lamson et al. | |
| 8,029,532 B2 | 10/2011 | Sirota | |
| 8,080,034 B2 | 12/2011 | Bates et al. | |
| 8,083,768 B2 * | 12/2011 | Ginn | A61B 17/0057 424/422 |
| 8,105,352 B2 | 1/2012 | Egnelov | |
| 8,114,124 B2 | 2/2012 | Buckman et al. | |
| 8,162,974 B2 * | 4/2012 | Eskuri | A61B 17/0057 606/213 |
| 8,211,122 B2 | 7/2012 | McIntosh | |
| 8,267,942 B2 | 9/2012 | Szabo et al. | |
| 8,277,481 B2 | 10/2012 | Kawaura et al. | |
| 9,943,302 B2 | 4/2018 | Bennett | |
| 2001/0003158 A1 | 6/2001 | Kensey et al. | |
| 2001/0046476 A1 | 11/2001 | Plochocka | |
| 2002/0188319 A1 | 12/2002 | Morris et al. | |
| 2002/0198562 A1 * | 12/2002 | Akerfeldt | A61B 17/0057 606/213 |
| 2003/0012734 A1 | 1/2003 | Pathak et al. | |
| 2004/0176800 A1 | 9/2004 | Paraschac et al. | |
| 2004/0185250 A1 | 9/2004 | John | |
| 2005/0065548 A1 * | 3/2005 | Marino | A61B 17/0057 606/213 |
| 2005/0085852 A1 * | 4/2005 | Ditter | A61B 17/0057 606/213 |
| 2005/0169974 A1 | 8/2005 | Tenerz et al. | |
| 2005/0234509 A1 * | 10/2005 | Widomski | A61B 17/0057 606/213 |
| 2005/0261709 A1 | 11/2005 | Sakamoto et al. | |
| 2005/0267533 A1 | 12/2005 | Gertner | |
| 2005/0273135 A1 * | 12/2005 | Chanduszko | A61B 17/0057 606/213 |
| 2005/0283187 A1 | 12/2005 | Longson | |
| 2006/0106418 A1 * | 5/2006 | Seibold | A61B 17/0057 606/213 |
| 2006/0122608 A1 | 6/2006 | Fallin et al. | |
| 2006/0142797 A1 | 6/2006 | Egnelov | |
| 2006/0173492 A1 | 8/2006 | Akerfeldt et al. | |
| 2006/0206146 A1 * | 9/2006 | Tenerz | A61B 17/0057 606/213 |
| 2006/0229670 A1 | 10/2006 | Bates | |
| 2006/0229672 A1 | 10/2006 | Forsberg | |
| 2006/0229673 A1 | 10/2006 | Forsberg | |
| 2006/0229674 A1 | 10/2006 | Forsberg | |
| 2006/0259074 A1 * | 11/2006 | Kelleher | A61B 17/0469 606/213 |
| 2006/0265006 A1 | 11/2006 | White et al. | |
| 2006/0265007 A1 | 11/2006 | White et al. | |
| 2007/0032823 A1 | 2/2007 | Tegg | |
| 2007/0032824 A1 | 2/2007 | Terwey | |
| 2007/0049971 A1 | 3/2007 | Chin et al. | |
| 2007/0135842 A1 | 6/2007 | Van de Moer et al. | |
| 2007/0150002 A1 * | 6/2007 | Szabo | A61B 17/0057 606/232 |
| 2007/0156175 A1 | 7/2007 | Weadock et al. | |
| 2007/0167982 A1 | 7/2007 | Gertner et al. | |
| 2007/0185529 A1 | 8/2007 | Coleman et al. | |
| 2007/0198059 A1 * | 8/2007 | Patel | A61L 27/3633 606/213 |
| 2007/0255314 A1 | 11/2007 | Forsberg | |
| 2007/0276433 A1 | 11/2007 | Huss | |
| 2008/0004657 A1 * | 1/2008 | Obermiller | A61B 17/0057 606/213 |
| 2008/0027477 A1 * | 1/2008 | Obermiller | A61B 17/0057 606/191 |
| 2008/0071310 A1 * | 3/2008 | Hoffman | A61B 17/0057 606/215 |
| 2008/0071311 A1 | 3/2008 | White et al. | |
| 2008/0114092 A1 | 5/2008 | Sawhney | |
| 2008/0114395 A1 | 5/2008 | Mathisen et al. | |
| 2008/0243182 A1 * | 10/2008 | Bates | A61B 17/0057 606/213 |

FOREIGN PATENT DOCUMENTS

| | | |
|---|---|---|
| EP | 2143737 A1 | 1/2010 |
| EP | 2153779 A2 | 2/2010 |
| EP | 2196193 A1 | 6/2010 |

(56) References Cited

FOREIGN PATENT DOCUMENTS

| | | | |
|---|---|---|---|
| EP | 2233160 | A2 | 9/2010 |
| EP | 2233161 | A2 | 9/2010 |
| FR | 2839451 | A1 | 11/2003 |
| WO | 9428800 | A1 | 12/1994 |
| WO | 2005016176 | A2 | 2/2005 |
| WO | 2005110280 | A2 | 11/2005 |
| WO | 2006009925 | A2 | 1/2006 |

OTHER PUBLICATIONS

International Search Report from Application No. EP 08 25 0526 dated Jan. 7, 2009.
European Search Report for EP 10251821.4-1269 date of completion is Jan. 25, 2011 (3 pages).
European Search Report for EP 12169360.0-1269 date of completion is Jun. 8, 2012 (6 pages).
International Search Report issued in Application EP 11250562.3 dated Dec. 8, 2011.
International Search Report issued in Application EP 11250564.9 dated Dec. 8, 2011.
International Search Report issued in Application EP 11250563.1 dated Dec. 27, 2011.
International Search Report issued in Application EP 11250566.4 dated Dec. 22, 2011.
International Search Report issued in Application EP 11250565.6 dated Dec. 23, 2011.
Raul Zurita et al.: "Triclosan Release from Coated Polyglycolide Threads", Macromolecular Bioscience, vol. 6, No. 1, Jan. 5, 2006, pp. 58-69.
European Search Report for EP 07751966 date of completion is Nov. 5, 2012.

* cited by examiner

MEDICAL DEVICE FOR WOUND CLOSURE AND METHOD OF USE

CROSS-REFERENCE TO RELATED APPLICATIONS

The present application is a divisional of U.S. patent application Ser. No. 12/511,462, filed on Jul. 29, 2009, now U.S. Pat. No. 9,943,302, which claims priority to, and the benefit of, U.S. Provisional Patent Application Ser. No. 61/088,145, filed on Aug. 12, 2008, the entire contents of each of which are hereby incorporated by reference.

BACKGROUND

Technical Field

The present disclosure relates to a medical device and more particularly a wound closure device for repairing perforations in tissue and sealing a tissue wall.

Background of Related Art

A variety of surgical procedures, for example, laparoscopic procedures, are performed through an access port, during which the access port punctures the tissue to provide access to the surgical site. Punctures, if left untreated for a period of time, may allow for fluid passage from one tissue/organ to another. Fluid passage between certain tissues may contribute to undesirable complications such as infection.

Currently, wound closure devices such as sutures are used to close various layers of tissue post-surgery. Suturing a patient after removal of an access device may be cumbersome, while accumulating additional costs to the patient such as increased time spent in the operating room.

It would be advantageous to provide a device which enables improved, e.g., faster, closure of tissue punctures or tissue perforations for certain procedures.

SUMMARY

A medical device for wound closure is described herein which provides for improved wound closure. In one embodiment, the medical device includes an elongate body having a plurality of barbs extending from a surface thereof, and an inner member and outer member, each moveably positioned along the elongate body.

In one embodiment, the inner member and outer member are each spaced from a distal portion of the elongate body. In use, the inner member is preferably moveably positionable between a tissue wall and the outer member. In certain embodiments, the inner member is a tissue scaffold. The outer member is preferably relatively rigid as compared to the inner member. The outer member may also serve as a tissue scaffold.

The medical device may also include a foam structure attached to the distal portion of the elongate body. Preferably, the foam structure is configured to change dimension from a first compressed shape for delivery to second expanded shape for placement. The foam structure may also be shaped so as to limit movement proximally through a tissue wall. In certain embodiments, the foam structure is a closed cell foam.

The elongate body preferably also includes a plurality of barbs which are oriented so as to enable the outer member to move distally along the elongate body while limiting proximal movement of the outer member.

Another embodiment of a medical device for wound closure disclosed herein includes an elongate body having a distal portion and a proximal portion, and a plurality of barbs extending from a surface thereof. The medical device further includes a foam structure attached to the distal portion of the elongate body and an outer member moveably positioned on the elongate body. In some embodiments, the medical device may also include a tissue scaffold moveably positioned on the elongate body. In situ, the tissue scaffold may be at least partially positioned in a tissue perforation.

Tissue scaffolds of the present disclosure may be selected from the group consisting of proteins, polysaccharides, polynucleotides, poly (α-hydroxy esters), poly (hydroxy alkanoates), poly (ortho esters), polyurethanes, polylactones, poly (amino acids), and combinations thereof.

A method of closing tissue is also disclosed, the method comprising the steps of positioning a medical device through a tissue wall such that a foam structure at a distal end of the medical device is adjacent an inner surface of the tissue; and, advancing an outer member distally over barbs on a surface of the elongate body so as to secure the medical device in situ.

An alternate method of closing tissue is disclosed, the method comprising the steps of inserting a medical device through a tissue wall, at least a portion of the medical device being contained within a sleeve; removing the sleeve such that a foam structure at a distal end of the medical device is positioned adjacent an inner surface of the tissue; and, advancing an outer member distally over barbs on a surface of the elongate body so as to secure the medical device in situ.

BRIEF DESCRIPTION OF DRAWINGS

Various preferred embodiments of the wound closure devices are described herein with reference to the drawings, in which.

DETAILED DESCRIPTION OF EMBODIMENTS

The present disclosure is directed to a medical, e.g., wound closure, device. The wound closure device includes an elongate body having a plurality of barbs extending from the surface. The device also includes an inner member and an outer member, each moveably positioned on a proximal portion of the elongate body. In certain embodiments, the wound closure device further includes a foam structure attached to a distal portion of the elongate body. In some embodiments, the inner member or the outer member may function as a tissue scaffold moveably positioned on the elongate body.

In the description that follows, the term "proximal" as used herein, means the portion of the device which is nearer to the user, while the term "distal" refers to the portion of the device which is further away from the user. The term "tissue" as defined herein means various skin layers, muscles, tendons, ligaments, nerves, fat, fascia, bone and different organs.

Figure 1:
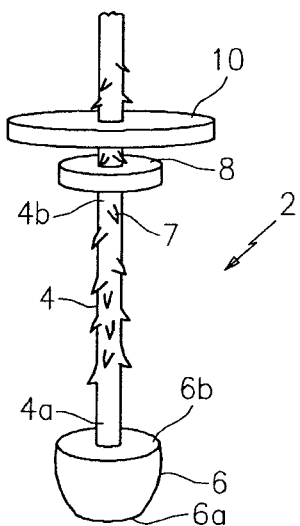
FIG. 1 is a perspective view of one embodiment of a wound closure device in accordance with the present disclosure.

A wound closure device according to one embodiment of the present disclosure is illustrated in FIG. 1. The wound closure device 2 comprises an elongate body 4 which includes a plurality of barbs 7 disposed along a surface of the elongate body 4. The elongate body 4 is generally cylindrical in shape and may have a generally circular cross-sectional area, although other shapes and cross-sectional areas are envisioned. In particular, the elongate body 4 is in the form of a suture and is comprised of a biodegradable polymeric material. A distal portion 4a of the elongate body 4 is connected to a foam structure 6. In particular, the elongate body 4 is centrally connected to a relatively flat surface 6b of the foam structure 6. Although shown centrally located, the elongate body 4 could also be attached off-center. The elongate body 4 may be connected to the foam structure 6 using various methods within the purview of those skilled in the art including, but not limited to, molding, over molding, adhesives and glues (e.g., cyanoacrylates), mechanical connections, male and female locking mechanisms, and the like.

As illustrated in FIG. 1, the foam structure 6 is generally conical or hemispherical in shape. A distal portion 6a of the foam structure 6 is generally arcuate in shape and once inserted through a tissue wall, the foam structure 6 is relatively convex with respect to a tissue wall. A proximal portion 6b of the foam structure 6 is generally flat and, in use, is positioned adjacent a tissue wall so as to seal a tissue perforation and prevent fluids from passing through a tissue wall or tissue plane. It should be noted that although the foam structure is illustrated as generally conical in shape, this disclosure is not limited to conical-shaped foam structures and other shapes are contemplated. The foam structure is large enough, for example, to extend over a tissue perforation created by an access device (e.g., endoluminal device), sealing the tissue wall and limiting fluid passage from a first side of a tissue wall to a second side of a tissue wall. It should also be noted that certain embodiments may not include a foam structure.

Foams of the present disclosure may be compressible and are capable of undergoing a change in shape. The foam structure may be of a configured to change shape from a first compressed shape when inserted in tissue for delivery to a second, expanded shape for placement. Upon penetration of a tissue wall, the foam structure may expand to seal a tissue defect. Foam structures of the present disclosure also are shaped so as to limit movement proximally through a tissue wall, once inserted. The foam structure may be constructed of a material which expands from heat or fluid (polymer hydrogels) contact; alternately, the foam structure may be mechanically compressed through use of a member such as a sleeve e.g., introducer, wherein upon removal of the sleeve, the foam expands. Other members including the outer member and the inner member may also be compressible foams which change shape from a first, smaller shape, to a second, larger shape.

Foams may have an open cell structure where the pores are connected to each other, forming an interconnected network. Conversely, foams of the present disclosure may be closed cell foams where the pores are not interconnected. Closed cell foams are generally denser and have a higher compressive strength. In certain preferred embodiments, the foam structure of the present disclosure is a closed cell foam.

Tissue damage or tissue voids may have the potential to form adhesions during certain healing periods. Foam structures of the present disclosure may be chemically tailored to have anti-adhesive properties, which may assist in preventing adjacent tissue walls from adhering together, preventing adhesions at a wound site. In various embodiments, the foam structures may be made of anti-adhesive materials. Alternatively, the foam structures may be coated with anti-adhesive materials.

Referring back to FIG. 1, the elongate body 4 has an inner member 8 and an outer member 10 mounted thereon. The inner member 8 and the outer member 10 are spaced from the distal portion 4a of the elongate body 4. In a preferred embodiment, the inner member 8 and the outer member 10 are located on the proximal portion 4b of the elongate body. Alternately, when the elongate body is longer in length, the inner member and outer member may be moveably mounted on a central portion of the elongate body. Each of the inner member 8 and outer member 10 has an opening extending therethrough and is moveably positioned on the elongate body 4. In situ, the inner member 8 is positioned between a tissue wall (not shown) and the outer member 10. Both the inner member 8 and the outer member 10 are generally shaped like a disc, although other shapes are envisioned. In some embodiments, the inner member 8 may be configured to fill a surface void or tissue defect. The outer member 10 is generally rigid as compared to the inner member 8 so as to affect movement of the inner member 8. In a preferred embodiment, the inner member 8 is comprised of an absorbable polymer such as collagen. The inner member 8 may be in the form of a sheet or a porous material such as foam. The outer member 10 may of any solid or dense porous material which is rigid, so as to impart movement on the inner member 8 as it is advanced distally along an elongate body 4.

In certain embodiments, at least the inner member 8 may provide a tissue scaffold for cellular infiltration and tissue ingrowth. It is also envisioned that in alternate embodiments, the outer member 10 may provide a scaffold for tissue ingrowth. The tissue scaffold is porous and provides a temporary scaffold/substrate for cell adherence. Tissue scaffolds may be tailored to closely match the mechanical properties of the surrounding tissue intended for regeneration. For example, when the wound closure device is used to close dermal tissue, the scaffold may be mechanically tuned to complement dermal tissue.

In preferred embodiments, the tissue scaffold comprises degradable materials including those listed below, and in certain preferred embodiments the tissue scaffold is collagen. The scaffold degradation profile can be tailored to allow cells to proliferate while the tissue scaffold degrades over time. One skilled in the art can alter the degradation profile of a tissue scaffold by changing various parameters including but not limited to polymer composition and chemistry, density, morphology, molecular weight, size, porosity and pore size, wettability and processing parameters.

As illustrated in FIG. 1, the elongate body 4 further includes a plurality of barbs 7 which may be aligned to enable the wound closure device 2 to move through tissue in one direction while resisting movement through tissue in a generally opposite direction. That is, the barbs 7, extending from the surface of the elongate body 4, permit movement of inner member 8 and outer member 10 in a distal direction while resisting movement of the inner member 8 and outer member 10 in a proximal direction. Additionally, the barbs 7 prevent movement of the foam structure 6 towards a proximal portion of the device. Once the foam structure 6 of the device 2 is positioned adjacent a tissue wall, the outer member 10 is advanced in a distal direction along the elongate body 4, thereby moving the inner member 8 in a distal direction (with the barbs preventing proximal movement). Once the inner member 8 and outer member 10 are fully distally advanced e.g., contacting a tissue wall, the barbs 7 prevent proximal movement of the inner and outer members (8 and 10), thereby fixating the device 2 against the tissue wall (not shown).

The term "barbs" as used herein encompasses various projections from the surface of an elongate body. Preferably the barbs are formed integrally with the elongate body 4. Barbs extending from the outer surface of the elongate body 4 include but are not limited to projections such as threads, anchors, and teeth. In some embodiments, the barbs are yieldable toward the elongate body 4 of the wound closure device. The barbs can be arranged in any suitable pattern, for example helical, linear, or randomly spaced. The number, configuration, spacing and surface area of the barbs can vary depending upon the tissue type in which the device is used, as well as the composition and geometry of the material utilized to form the device. For example, if the wound closure device is intended to be used in fatty tissue, which is relatively soft, the barbs may be longer and spaced further apart to enable it to grip the soft tissue. The barbs can be arranged in various directions at various angles. In some embodiments, the wound closure device may include a staggered arrangement of large or small barbs.

The shape and/or surface area of the barbs can also vary. For example, fuller-tipped barbs can be made of varying sizes designed for specific surgical applications. In certain applications, such as when closing an access port site and the surgeon is working with fat and relatively soft tissues, larger barbs may be desired, whereas smaller barbs may be more suitable for different procedures with collagen-dense tissues. In some embodiments, a combination of large and small barbs within the same structure may be beneficial, for example when a wound closure device is used in tissue repair with differing layer structures. Use of the combination of large and small barbs on the same device, wherein barb sizes are customized for each tissue layer will ensure maximum holding strength of the device in situ.

Figure 2A:
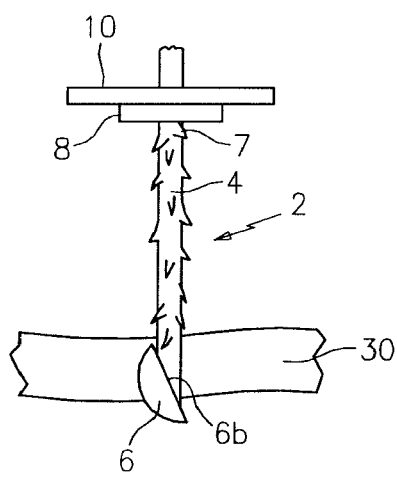
FIGS. 2A-2D are side views of the device of FIG. 1, with portions of tissue removed, showing the steps of placement of the device.
Figure 2B:
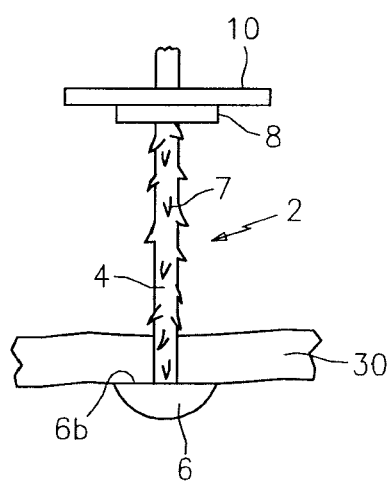

FIGS. 2A and 2B illustrate according to one embodiment, a method by which the wound closure device of FIG. 1 may be positioned in tissue. Note, portions of the tissue are removed for clarity. In FIG. 2A, a device 2 is shown in a first position where a foam structure 6 has partially penetrated a tissue wall 30. The device may be inserted into tissue and a distal portion of the device 2 may be inserted through a tissue wall 30 with or without the use of an inserter (not shown). Once the device 2 is completely inserted and the foam structure 6 has fully penetrated the tissue wall 30, the proximal portion 6b of the foam structure 6 may be rotated (by the user or an insertion device) for positioning against the tissue wall 30 (FIG. 2B). The proximal portion 6b of the foam structure 6, which may be generally flat, is positioned adjacent a tissue wall 30 so as to seal a puncture wound and prevent fluids from passing through the tissue wall or tissue plane. It should be noted that the foam structure 6 may be inserted in a position so as to minimize tissue contact during delivery. As shown in FIG. 1, the foam structure 6 is inserted at an angle and rotated or turned into position against a tissue wall 30; in other embodiments, an inserter may to used which enables the foam structure 6 to be inserted in a compressed position so as to minimize tissue contact during delivery.

Figure 2C:
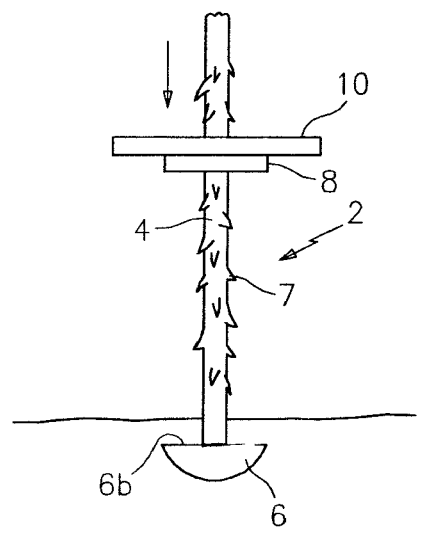
Figure 2D:
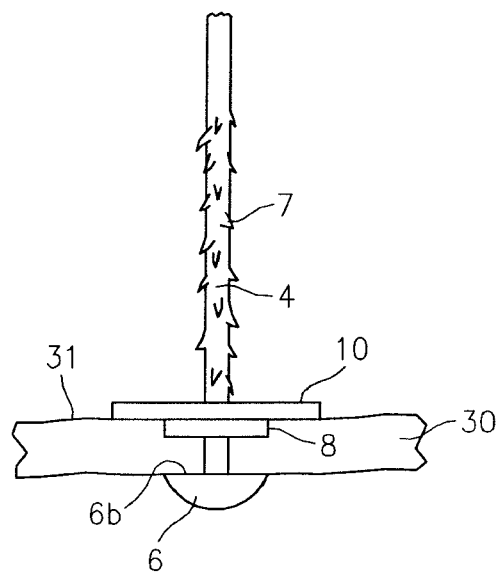

In the next step, an outer member 10 is advanced in a distal direction as indicated by an arrow in FIG. 2C. As previously described, the outer member 10 may be rigid as compared to an inner member 8, and its movement imparts movement of the inner member 8. That is, the outer member 10 is advanced towards the inner member 8 and once in contact, the outer member 10 and the inner member 8 move together over the barbed surface 4 in a distal direction so as to secure the device 2 in tissue (FIG. 2D). In a final position, the inner member 8 is adjacent a tissue surface 31, applying pressure to the tissue surface 31 so as to limit movement of the device 2. As the inner member 8 and the outer member 10 are advanced over the barbed surface 4, the barbs 7 inhibit movement of the inner and outer members (8, 10) in a proximal direction. The barbs 7 may also prevent the foam structure 6 from reversible movement after penetration of the tissue wall 30. It should be noted that although FIGS. 2A-2D illustrate the embodiment described in FIG. 1, other embodiments described herein will be placed in tissue in a similar manner.

Figure 3:
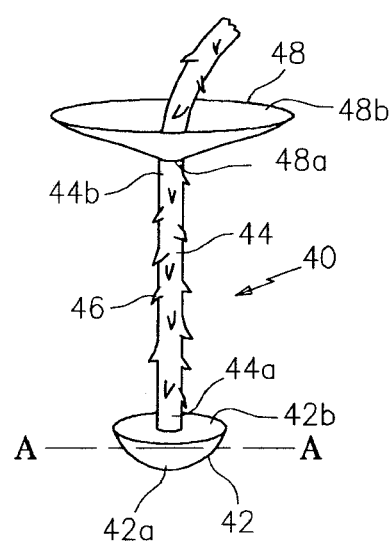
FIG. 3 is an alternate embodiment of a wound closure device in accordance with the present disclosure.
Figure 4:
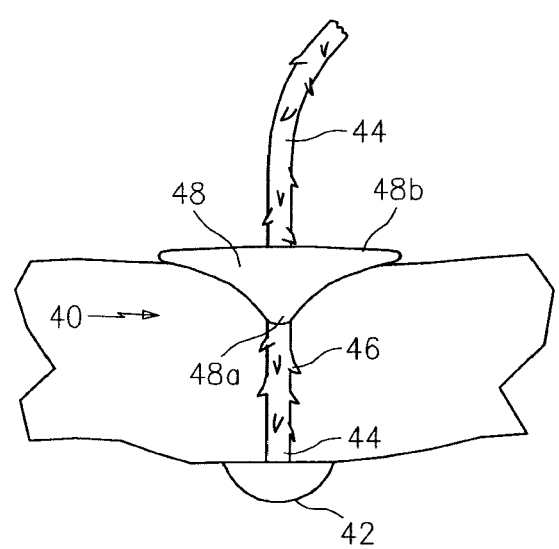
FIG. 4 is a side view of the device of FIG. 3, with portions of tissue removed, showing the device in tissue.

Another embodiment of a wound closure device 40 is shown in FIG. 3. An elongate body 44 is connected at a distal portion 44a to a foam structure 42 the elongate body 44 has an outer member 48 mounted thereon, spaced from a distal portion 44a of the elongate body. The foam structure 42 may be generally conical or hemispherical in shape, having a generally flat proximal portion 42b and a curved or somewhat pointed distal portion 42a. The foam structure 42 is circular in cross-sectional area, taken along line A-A, although other shapes are envisioned. The foam structure 42 may be centrally attached to a barbed elongate body 44, or could alternatively be attached off-center. The barbs 46 function in a similar manner as described above and may have various lengths and may be disposed at different angles relative to a surface of the elongate body 44. The outer member 48 has an opening extending therethrough and is rigid enough to move in a distal direction over the barbed elongate body 44. The outer member 48 as shown is funnel-shaped such that a proximal portion 48b has a larger cross-sectional area, which narrows toward a distal portion 48a. In situ, the distal portion 48a may partially penetrate a tissue plane, as illustrated in FIG. 4. The funnel shape of the outer member 48 may assist in further sealing of a tissue defect which may be created by an access device such as an endoscopic device used for Natural Orifice Transluminal Endoscopic Surgery (N.O.T.E.S.). In certain embodiments, the outer member may further include an active agent such as a hemostat.

Figure 5A:
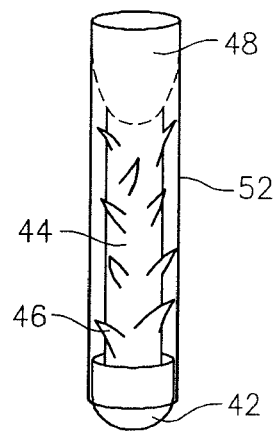
FIG. 5A is a side view of the device of FIG. 3 in a first, compressed shape; and, FIG. 5B is a side view of the device of FIG. 3 in tissue, with portions of tissue removed, in a second, expanded shape.
Figure 5B:
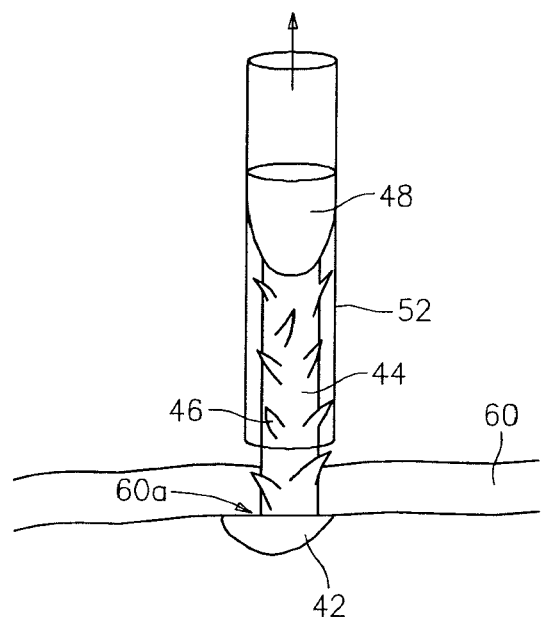

Wound closure devices of the present disclosure may be inserted with the assistance of an introducer (insertion device). FIG. 5A illustrates the embodiment of FIGS. 3 and 4 by way of example, it being understood that other embodiments of a wound closure device as described herein may also be compressed by a sleeve for insertion into tissue. The sleeve 52 may be employed to retain the foam structure 42 in a first, compressed shape for insertion/delivery. The sleeve 52 also extends over the elongate body 44 and outer member 48. Upon penetrating a tissue wall 60 (FIG. 5B), the sleeve 52 may be removed (retracted in the direction of the arrow), allowing the foam structure 42 to expand to a second larger shape, extending over a tissue defect 60a, for placement. Once the sleeve is removed, the outer member 48 may be advanced in a distal direction, securing the device in place. The sleeve may also keep other members of the device, e.g., inner members and tissue scaffolds, in a compressed position for insertion into a body cavity.

Materials used to construct the wound closure devices of the present disclosure may include biodegradable materials which may be synthetic and natural materials. The term "biodegradable" as used herein refers to materials which decompose, or lose structural integrity under body conditions (e.g., enzymatic degradation or hydrolysis). Suitable synthetic biodegradable materials may include, but are not limited to, polymers such as those made from lactide, glycolide, caprolactone, valerolactone, carbonates (e.g., trimethylene carbonate, tetramethylene carbonate, and the like), dioxanones (e.g., 1,4-dioxanone), δ-valerolactone, 1,dioxepanones (e.g., 1,4-dioxepan-2-one and 1,5-dioxepan-2-one), ethylene glycol, ethylene oxide, esteramides, γ-hydroxyvalerate, β-hydroxypropionate, alpha-hydroxy acid, hydroxybuterates, poly (ortho esters), hydroxy alkanoates, tyrosine carbonates, polyimide carbonates, polyimino carbonates such as poly (bisphenol A-iminocarbonate) and poly (hydroquinone-iminocarbonate), polyurethanes, polyanhydrides, polymer drugs (e.g., polydiflunisol, polyaspirin, and protein therapeutics) and copolymers and combinations thereof.

In certain preferred embodiments, the foam structure comprises a material which contains an aliphatic diacid linking two dihydroxy compounds. The dihydroxy compounds which may be utilized include, but are not limited to, polyols including polyalkylene oxides, polyvinyl alcohols, and the like. In some embodiments, the dihydroxy compounds can be a polyalkylene oxide such as polyethylene oxide ("PEO"), polypropylene oxide ("PPO"), block or random copolymers of polyethylene oxide (PEO) and polypropylene oxide (PPO). Suitable aliphatic diacids which may be utilized in forming the foams include, for example, aliphatic diacids having from about 2 to about 8 carbon atoms suitable diacids include, but are not limited to sebacic acid, azelaic acid, suberic acid, pimelic acid, adipic acid, glutaric acid, succinic acid, malonic acid, oxalic acid and combinations thereof.

In one embodiment, a polyethylene glycol ("PEG") may be utilized as the dihydroxy compound as disclosed in U.S. Patent Application Publication No. 20060253094, the entire disclosure of which is incorporated by reference herein. It may be desirable to utilize a PEG with a molecular weight ranging from about 200 to about 1000, typically from about 400 to about 900. Suitable PEGs are commercially available from a variety of sources under the designations PEG 200, PEG 400, PEG 600 and PEG 900.

Suitable natural biodegradable polymers may include, but are not limited to, collagen, poly (amino acids), polysaccharides such as cellulose, dextran, chitin, and glycosaminoglycans, hyaluronic acid, gut, copolymers and combinations thereof. In preferred embodiments, collagen is used to construct the inner member of the medical device. Collagen as used herein includes natural collagen such as animal derived collagen, or synthetic collagen such as human or bacterial recombinant collagen.

The collagen can be modified by using any method known to those skilled in the art to provide pendant portions of the collagen with moieties which are capable of covalently bonding with the reactive chemical groups of a glycosaminoglycan. Examples of such pendant moieties include aldehydes, sulfones, vinylsulfones, isocyanates, and acid anhydrides. In addition, electrophilic groups such as —$CO_2N$ $(COCH_2)_2$, —$CO_2N(COCH_2)_2$, —$CO_2H$, —CHO, —$CHOCH_2$, —N=C=O, —$SO_2CH$=$CH_2$, —$N(COCH_2)_2$, —S—S—($C_5H_4N$) may also be added to pendant chains of the collagen to allow covalent bonding to occur with the glycosaminoglycans.

In some embodiments, the collagen may be modified through the addition of an oxidizing agent. Contacting collagen with an oxidizing agent creates oxidative cleavage along portions of the collagen thereby creating pendant aldehyde groups capable of reacting with the glycosaminoglycans. The oxidizing agent may be, for example, iodine, peroxide, periodic acid, hydrogen peroxide, a periodate, a compound containing periodate, sodium periodate, a diisocyanate compound, a halogen, a compound containing halogen, n-bromosuccinimide, a permanganate, a compound containing permanganate, ozone, a compound containing ozone, chromic acid, sulfuryl chloride, a sulfoxide, a selenoxide, an oxidizing enzyme (oxidase) and combinations thereof. In certain embodiments, the oxidizing agent is periodic acid.

In certain applications it may be preferred to have certain members of the wound closure device comprise non-degradable materials. For example, in applications where a wound closure device is used for dermal closure, it may be beneficial for the outer member to be non-degradable. A non-degradable material may be better suited for an external environment, or may provide better resistance against skin flora, compared to certain biodegradable materials.

Suitable non-biodegradable materials may be used to construct the wound closure device including, but not limited to, fluorinated polymers (e.g., fluoroethylenes, propylenes, fluoroPEGs), polyolefins such as polyethylene, polyesters such as poly ethylene terepththalate (PET), nylons, polyamides, polyurethanes, silicones, ultra high molecular weight polyethylene (UHMWPE), polybutesters, polyethylene glycol, polyaryletherketone, copolymers and combinations thereof. Additionally, non-biodegradable polymers and monomers may be combined with each other and may also be combined with various biodegradable polymers and monomers to create a composite device.

In certain embodiments, medical devices according to the present disclosure may be constructed at least in part using shape memory polymers. Suitable polymers used to prepare hard and soft segments of shape memory polymers may include, but are not limited to, polycaprolactone, dioxanone, lactide, glycolide, polyacrylates, polyamides, polysiloxanes, polyurethanes, polyether amides, polyurethane/ureas, polyether esters, and urethane/butadiene copolymers and combinations thereof. For example, the foam structure may comprise shape memory materials which expand the foam upon reaching body temperature, sealing an inner tissue wall.

In some embodiments, the medical device may comprise metals (e.g., steel or titanium), metal alloys and the like. In alternate embodiments, the elongate body or outer member may comprise degradable metals such as degradable magnesium.

Suitable materials of the present disclosure can be processed by methods within the purview of those skilled in the art including, but not limited to extrusion, injection molding, compression molding, blow molding, film blowing, thermoforming, calendaring, spinning, and film casting.

More specifically, foams of the present disclosure can be manufactured using various processes within the purview of those skilled in the art. For example, foams can be manufactured though standard lyophilization (freeze drying) techniques, solvent casting and particulate leaching, compression molding, phase separation, gas foaming (e.g., internal blowing agents such as $CO_2$), or through the use of a porogen (e.g., salt particles). In certain embodiments, foams which are used as tissue scaffolds can also be created through computer aided design techniques including solid freeform fabrication (SFF).

Additionally, any part of the device may include biologically acceptable additives such as plasticizers, antioxidants, dyes, image-enhancing agents, dilutants, bioactive agents such as pharmaceutical and medicinal agents, and combinations thereof which can be coated on the wound closure device or impregnated within the resin or polymer.

Medicinal agents which may be incorporated into the wound closure device may include, but are not limited to, antimicrobial agents, anti-virals, anti-fungals, and the like. Antimicrobial agents as used herein is defined by an agent which by itself or through assisting the body (immune system) helps the body destroy or resist microorganisms which may be pathogenic (disease causing). The term "antimicrobial agent" includes, e.g., antibiotics, quorum sensing blockers, surfactants, metal ions, antimicrobial proteins and peptides, antimicrobial polysaccharides, antiseptics, disinfectants, anti-virals, anti-fungals, quorum sensing blockers, and combinations thereof.

Examples of suitable antiseptics and disinfectants which may be combined with the present disclosure include hexachlorophene; cationic biguanides like chlorohexadine and cyclohexidine; iodine and iodophores like povidone-iodine; halo-substituted phenolic compounds like PCMX (e.g., p-chloro-m-xylenon) and triclosan (e.g., 2,4,4'-trichloro-2'hydroxy-diphenylether); furan medical preparations like nitrofurantoin and nitrofurazone; methanamine; aldehydes like gluteraldehyde and formaldehyde; alcohols; combinations thereof, and the like. In some embodiments, at least one of the antimicrobial agents may be an antiseptic, such as triclosan.

Classes of antibiotics that can be combined with the present disclosure include tetracyclines like minocycline; rifamycins like rifampin; macrolides like erythromycin; penicillins like nafcillin; cephalosporins like cefazolon; beta-lactam antibiotics like imipenen and aztreonam; aminoglycosides like gentamicin and TOBRAMYCIN®; chloramphenicol; sulfonamides like sulfamethoxazole; glycopeptides like vancomycin; quilones like ciproflaxin; fusidic acid; trimethoprim; metronidazole; clindamycin; mupirocin; polyenes like amphotericin B; azoles like fluconazole; and beta-lactam inhibitors like sublactam. Other antimicrobials which may be added include, for example antimicrobial peptides and/or proteins; antimicrobial polysaccharides; quorum sensing blockers (e.g., brominated furanones); anti-virals; metal ions such as ionic silver and ionic silver glass; surfactants; chemotherapeutic drug; telomerase inhibitors; other cyclic monomers including 5-cyclic monomers; mitoxantrone; and the like.

In some embodiments, suitable bioactive agents which may be used include colorants, dyes, preservatives, protein and peptide preparations, protein therapeutics, polysaccharides such as hyaluronic acid, lectins, lipids, probiotics, angiogenic agents, anti-thrombotics, anti-clotting agents, clotting agents, analgesics, anesthetics, wound repair agents, chemotherapeutics, biologics, anti-inflammatory agents, anti-proliferatives, diagnostic agents, antipyretic, antiphlogistic and analgesic agents, vasodilators, antihypertensive and antiarrhythmic agents, hypotensive agents, antitussive agents, antineoplastics, local anesthetics, hormone preparations, antiasthmatic and antiallergic agents, antihistaminics, anticoagulants, antispasmodics, cerebral circulation and metabolism improvers, antidepressant and antianxiety agents, vitamin D preparations, hypoglycemic agents, anti-ulcer agents, hypnotics, antibiotics, antifungal agents, sedative agents, bronchodilator agents, antiviral agents, dysuric agents, brominated or halogenated furanones, and the like. In embodiments, polymer drugs, e.g., polymeric forms of such compounds for example, polymeric antibiotics, polymeric antiseptics, polymeric chemotherapeutics, polymeric anti-proliferatives, polymeric antiseptics, polymeric non-steroidal anti-inflammatory drugs (NSAIDS), and the like may be utilized and combinations thereof.

In certain embodiments, medical devices of the present disclosure may contain suitable medicinal agents such as viruses and cells; peptides; polypeptides and proteins, analogs, muteins, and active fragments thereof, such as immunoglobulins; antibodies (monoclonal and polyclonal); cytokines (e.g., lymphokines, monokines, chemokines); blood clotting factors; hemopoietic factors; interleukins (IL-2, IL-3, IL-4, IL-6); interferons ($\beta$-IFN, $\alpha$-IFN and $\gamma$-IFN); erythropoietin; nucleases; tumor necrosis factor; colony stimulating factors (e.g., GCSF, GM-CSF, MCSF); insulin; anti-tumor agents and tumor suppressors; blood proteins; gonadotropins (e.g., FSH, LH, CG, etc.); hormones and hormone analogs (e.g., growth hormone); vaccines (e.g., tumoral, bacterial and viral antigens); somatostatin; antigens; blood coagulation factors; growth factors; protein inhibitors; protein antagonists and protein agonists; nucleic acids, such as antisense molecules, DNA, RNA, oligonucleotides, polynucleotides and ribozymes and combinations thereof.

In some embodiments, additives such as image-enhancing agents (e.g., contrast agents) and more specifically, radiopaque markers, may be incorporated into the medical device. These image-enhancing agents enable visualization of the wound closure device (against surrounding tissue), when imaged or scanned through different filters such as MRI, X-ray, fluoroscopy, CT, various light sources, and the like. In order to be opaque (and visualized in certain filters), the wound closure device may be made from a material possessing radiographic density higher than the surrounding host tissue and have sufficient thickness to affect the transmission of x-rays to produce contrast in the image. Useful image-enhancing agents include but are not limited to radiopaque markers such as tantalum, barium sulfate, bismuth trioxide, bromine, iodide, titanium oxide, zirconium, barium, titanium, bismuth, iodine, nickel, iron, silver, and combinations thereof. In some embodiments, compounds such as tantalum, platinum, barium and bismuth may be incorporated into the wound closure device. Often image-enhancing agents are not bioabsorbable or degradable but are excreted from the body or stored in the body.

Image-enhancing agents may be compounded into the materials (e.g., resin) as filler prior to processing including extrusion or molding. These agents may be added in various concentrations to maximize polymer processing while maximizing the material characteristics of the wound closure device. The biocompatible agents can be added in quantities sufficient to enhance radiopacity while maintaining the polymer's properties. In certain embodiments, image-enhancing agents may be incorporated into a biodegradable material, enabling surgeons to know when the biodegradable material has degraded.

Methods for combining the above mentioned bioactive agents with materials of the present disclosure are within the purview of those skilled in the art and include, but are not limited to mixing, blending, compounding, spraying, wicking, solvent evaporating, dipping, brushing, vapor deposition, coextrusion, capillary wicking, film casting, molding and the like. Additionally, solvents may be used to incorporate various agents (e.g., bioactive agents) into the composite device. Suitable solvents include alcohols, e.g., methanol, ethanol, propanol, chlorinated hydrocarbons (such as methylene chloride, chloroform, 1,2-dichloro-ethane), and aliphatic hydrocarbons such as hexane, heptene, ethyl acetate.

The above description contains many specifics; these specifics should not be construed as limitations on the scope of the disclosure herein but merely as exemplifications of particularly useful embodiments thereof. Those skilled in the art will envision many other possibilities within the scope and spirit of the disclosure as defined by the claims appended hereto.

What is claimed is:

1. A method of closing tissue, the method comprising:
    inserting a medical device through a tissue wall, the medical device having an elongate body including barbs extending from a surface thereof, a foam structure secured to a distal end of the elongate body, and an outer member disposed on the elongate body distal to a proximal end of the elongate body and moveably positioned therealong such that the medical device is inserted through the tissue wall with the elongate body, the foam structure, and the outer member all connected together, the outer member and the foam structure each having a proximal portion tapering towards a distal portion;
    positioning the medical device in the tissue wall such that the proximal portion of the foam structure is adjacent to an inner surface of the tissue wall; and
    advancing the outer member of the medical device distally over the barbs of the elongate body and penetrating the tissue wall with the distal portion of the outer member so as to secure the medical device in situ.

2. The method of claim 1, wherein the foam structure of the medical device includes a flat surface, and wherein positioning the medical device includes positioning the flat surface of the foam structure against the inner surface of the tissue wall.

3. The method of claim 1, wherein inserting the medical device includes inserting the foam structure of the medical device at an angle with respect to the elongate body.

4. The method of claim 3, wherein positioning the medical device includes turning the foam structure into position against the inner surface of the tissue wall.

5. The method of claim 3, wherein inserting the foam structure includes inserting the foam structure directly through the tissue wall without the use of an insertion device.

6. The method of claim 1, wherein advancing the outer member includes positioning the outer member adjacent an outer surface of the tissue wall.

7. The method of claim 1, wherein advancing the outer member includes positioning the proximal portion of the outer member against an outer surface of the tissue wall.

8. A method of closing tissue, the method comprising:
    inserting a medical device through a tissue wall, the medical device including an elongate body having an outer member moveably positioned on the elongate body and a foam structure disposed at a distal end of the elongate body, the outer member and the foam structure each having a proximal portion tapering towards a distal portion, and the outer member, the foam structure, and at least a portion of the elongate body contained within a sleeve;
    removing the sleeve such that the foam structure at the distal end of the medical device is positioned adjacent an inner surface of the tissue wall; and
    advancing the outer member of the medical device distally over barbs on a surface of the elongate body and penetrating the tissue wall with the distal portion of the outer member so as to secure the medical device in situ.

9. The method of claim 8, wherein the foam structure of the medical device includes a flat surface, and wherein removing the sleeve includes positioning the flat surface of the foam structure against the inner surface of the tissue wall.

10. The method of claim 8, wherein the foam structure is contained within the sleeve in a compressed shape, and wherein removing the sleeve includes expanding the foam structure to an expanded shape.

11. The method of claim 8, wherein the outer member is contained within the sleeve in a compressed shape, and wherein removing the sleeve includes expanding the outer member to an expanded shape.

12. The method of claim 2, wherein advancing the outer member includes positioning the outer member adjacent an outer surface of the tissue wall.

13. The method of claim 8, wherein advancing the outer member includes positioning the proximal portion of the outer member against an outer surface of the tissue wall.

* * * * *